United States Patent [19]

Coelho et al.

[11] Patent Number: 5,261,255
[45] Date of Patent: Nov. 16, 1993

[54] DEVICE FOR FRACTIONATING CONSTITUENT COMPONENTS OF A SUBSTANCE USING CRYOPRECIPITATION

[75] Inventors: Philip H. Coelho; Terry Wolf, both of Rancho Cordova, Calif.

[73] Assignee: Instacool Inc. of North America, Rancho Cordova, Calif.

[21] Appl. No.: 789,293

[22] Filed: Nov. 8, 1991

[51] Int. Cl.$^5$ .................. F25D 17/02; C07G 7/00
[52] U.S. Cl. .......................... 62/376; 62/62; 62/68; 604/113; 604/19
[58] Field of Search ............ 62/63, 64, 373, 374, 62/375, 376, 68; 392/470; 128/276

[56] References Cited

U.S. PATENT DOCUMENTS

| | | | |
|---|---|---|---|
| 2,845,929 | 8/1958 | Strumia | 128/276 |
| 2,914,445 | 11/1959 | Clarke | 167/74 |
| 3,027,734 | 4/1962 | Mills | 62/375 |
| 3,586,097 | 6/1971 | Bender et al. | 392/470 X |
| 4,025,618 | 5/1977 | Garber et al. | |
| 4,129,131 | 12/1978 | Naftulin | 128/276 |
| 4,638,048 | 1/1987 | Foster | 530/380 |
| 4,707,587 | 11/1987 | Greenblatt | 392/470 X |
| 4,715,195 | 12/1987 | Kucza | 62/376 |

FOREIGN PATENT DOCUMENTS

| | | | |
|---|---|---|---|
| 137147 | 10/1979 | Japan | 62/374 |
| 2180754 | 8/1987 | Japan | 604/113 |
| 2014583 | 8/1979 | United Kingdom . | |

OTHER PUBLICATIONS

1990 Flash System and Related Products Catalog, Lifesource Advanced Blood bank Systems, Atlanta, Ga.
Farrugia, A.; Prowse, C. *J. Clin. Pathol.* 1985; 38:433–437.

*Primary Examiner*—Henry A. Bennet
*Assistant Examiner*—Chris Kilner
*Attorney, Agent, or Firm*—Bernhard Kreten

[57] ABSTRACT

A method and device for fractionating pouches of cryoprecipitable material including a membrane which provides a barrier within an interior of the device with the membrane receiving the pouches of cryoprecipitable material therewithin. The interior of the device includes a sump having a heat transfer fluid stored therein and maintained at a temperature which is to be achieved by the cryoprecipitable material as it cycles between freezing and thawing. The pouch of material, after placement within the membrane, is exposed (through the membrane) to hydrostatic forces associated with the heat transfer fluid in the sump collapsing the membrane on the pouch while pulsating jets impinge indirectly upon the pouch through the membrane. In this way, as the contents within the pouch change temperature, circulation of the fluid within the pouch occurs for more rapid realization of the cycling target temperatures for the cryoprecipitable material within the pouch. In one form, a single sump includes both a heating and cooling element for cycling the heat transfer fluid. In another form, two separate sumps respectively store "hot" heat transfer fluid and "cold" heat transfer fluid for alternate cycling. After plural cycles, the fractionated component of cryoprecipitable material is centrifuged and then separated.

15 Claims, 6 Drawing Sheets

DEVICE FOR FRACTIONATING CONSTITUENT COMPONENTS OF A SUBSTANCE USING CRYOPRECIPITATION

FIELD OF THE INVENTION

This invention relates generally to instrumentalities which can fractionate constituent components of substances such as blood, platelets or plasma using cryoprecipitation and a method therefore.

More specifically, the present invention relates to an improved method and apparatus for preparing fibrinogen concentrate. This invention also relates to the preparation of fibrinogen concentrate product which has clinical application as fibrin glue.

BACKGROUND OF THE INVENTION

Sutures have been used as a conventional surgical means for uniting tissues and surgical margins, as hemostatic aids, and for blocking or ligation. However, sutures suffer from many drawbacks. For example, sutures may be incompatible with the tissue, causing fistula or granuloma, sutures may cut through parenchymal and inflammatory tissues, absorbable suture material may disintegrate prematurely and produce dehiscence of the wound, and closely spaced sutures may cause tissue ischemia resulting in necrosis of the wound margins. Suturing is also time-consuming.

In order to overcome the above-mentioned shortcomings of sutures, various attempts at developing suitable substitutes have been made. One goal has been the development of a tissue glue which ensures union of the tissue without causing any damage thereto.

Cyanoacrylate-based substances have been commonly used as a fibrin glue. However, these substances are toxic to the tissue and cannot be absorbed (J. A. Collins, et al., "Cyanoacrylate Adhesives as Topical Hemostatic Aids", Surgery 65, 260–263, 1969). Thus, this type of tissue glue was found to result in the growth of granulated tissue in response to the foreign substance, rejection of the cyanoacrylate, fistula formation and local suppuration.

As early as 1909, it was realized that "fibrin powder" could be utilized to achieve blood clotting and wound healing (H. Matras, "Fibrin Seal: The State of the Art", J. Oral Maxillofac Surg 43, 605–611, 1985). Others later used fibrin tampons and thin fibrin plaques to control bleeding in parenchymal organs (see, e.g., E. G. Grey, "Fibrin as a Hemostatic in Cerebral Surgery", Surg Gynecol Obstet 21, 452–454, 1915). Another attempt involved the uniting of rabbit nerve with chicken plasma and chicken embryo extract (J. Z. Young, et al., "Fibrin Suture of Peripheral Nerves", Lancet 239, 126–128, 1940). Other work involved autologous and homologous rabbit plasma (I. M. Tarlov, et al., "Plasma Clot and Silk Suture of Nerves", Surg Gynecol Obstet 76, 366–369, 1943). In 1944 the first use was made of a combination of fibrinogen and thrombin for anchoring skin grafts, but the results failed to demonstrate a good adhesive effect (see E. P. Cronkite, et al., "Use of Thrombin and Fibrinogen in Skin Grafting", JAMA 124, 976–980, 1944, and R. T. Tedrick, et al., "Fibrin Fixation of Skin Transplants", Surgery 15, 90–93, 1944).

Due to advances in basic research, it is now possible to prepare highly concentrated plasma products and isolate some coagulation factors. Rabbit cryoprecipitate solution and an equal amount of thrombin solution have been used together with fascicular adaptation to reunite a rabbit nerve stump. This procedure was later applied on a human. In the human application, autologous plasma cryoprecipitate solution was first used, but since the clottable substances were found to be insufficient, homologous cryoprecipitate solution from pooled single-donor plasmas was subsequently used to obtain higher concentration for better tensile strength. Later, fibrin glue or sealant became more widely known.

Fibrin glue or sealant was successfully adapted for use in microvascular surgery. Others later combined suturing and sealing when applying the procedure in neurosurgery for extra-intracranial anastamosis, and on the dura repair, satisfactory results were obtained using fibrin sealant.

Fibrin sealant has three components: fibrinogen concentrate, calcium chloride and thrombin. These components mimic the final common pathway of the clotting cascade, i.e. the conversion of fibrinogen to fibrin (see, e.g., R. W. Colman, et al., *Hemostasis & Thrombosis* (2d ed.), 1987). In vitro, fibrinogen induces adhesion, spreading, and microfilament organization of human endothelial cells. Fibrinogen also has been found to stimulate fibroblast growth. The surface protein of fibroblasts has been found to contain fibronection.

Various publications discuss the clinical applications of fibrin sealant, but only a few mention the binding or tensile strength of the fibrin sealant (see, e.g. Jorgensen, et al., "Mechanical Strength in Rat Skin Incisional Wounds Treated with Fibrin Sealant", J. Surg Research 42, 237–241, 1987 and Bense, et al., "Effect of Fibrin Sealant on the Tensile Strength of Rat Visceral Pleura", Scand J. Thor Cardiovasc Surg 21, 179–180, 1987). Heretofore, there has also been a lack of data concerning the required concentration of fibrinogen for tissue binding and the necessary tensile strength at this fibrinogen concentration for use in various tissues.

In preparing fibrin sealant, thrombin of bovine origin is diluted with calcium chloride, with concentrations dependent on the tissue to be applied and the time of clotting. Equal amounts of fibrinogen concentrate and thrombin diluted in calcium chloride are used for clinical application. When the two components are mixed, thrombin converts fibrinogen to fibrin so that clotting is initiated and the mixture solidified. Meanwhile, in the presence of calcium ions, thrombin activates factor XIII to factor XIIIa. Activated factor XIIIa together with thrombin catalyzes the crosslinkage of fibrin and increases the strength of the clot. During would healing the clot material undergoes gradual lysis and is completely absorbed.

A major application of fibrin sealant is in surgery as a hemostasis aid, especially in thoracic-cardiovascular surgery, and in traumatic surgery (liver or spleen injury). In other areas of medicine, fibrin sealant is used as a tool to facilitate hemostasis, permit tissue fixation, enhance implant material growth, stimulate fibroblast growth and as an embolization material. Applications include orthopedic surgery, neural surgery, periodontal surgery, cerebral surgery, sinus or fistula obturation in proctologic and general surgery, chest surgery and genitourinary surgery, skin grafting in burn patients, punch hair grafting in plastic surgery, closure of corneal incisions in eye surgery, repair of lymph leak in general surgery and in myringoplasty in ear surgery.

Although there are great advantages to using fibrin sealant in clinical medicine, it is prohibited to use the commercially available product from pooled human plasma in the United States because of potential transmission of hepatitis B, acquired immunodeficiency syndrome (AIDS), and other transfusion transmittable diseases. The Food and Drug Administration (FDA) regulations have required that all plasma protein fractions shall receive heat treatment for not less than 10 or more than 11 hours at an attained temperature of $60° +/- 0.5°$ C. to inactivate infectious agents.

Commercially available fibrinogen is prepared from the plasma pooling of a large number of donors, which has high potential for disease transmission. In addition, fibrinogen will not tolerate the ten hours of heating to 60° C. used to inactivate the hepatitis virus in other blood fractions. Studies have indicated that this product was a source of hepatitis transmission (7.8% of post-transfusion hepatitis rate). Under these circumstances, the FDA revoked all licenses for the manufacture of human fibrinogen since Jun. 30, 1978.

In Europe, fibrinogen product is commercially available as a fibrinogen concentrate kit ("Tisseel", Immonu AG, Vienna, Austria) prepared from pooled fresh frozen plasma. The tensile strength for Tisseel is $900/g/cm^2$. Since this commerical fibrinogen concentrate is not available in the United States because it is currently not licensed by the FDA, alternative methods such as chemical precipitation and cryoprecipitation have been used to prepare fibrinogen concentrate.

Fibrinogen is one of the three main protein constituents of plasma. The major constituent, albumin (ALB), occurs in a concentration of approximately four percent. The plasma globulins are present in a concentration of about 2.5 percent and are particularly associated with the processes of immunity. Fibrinogen occurs in much smaller amounts, with its concentration in human plasma being about 0.4 percent.

Several authors have discussed fibrinogen/fibrinogen interaction and fibrinogen interaction with other proteins. Aggregation of fibrinogen at pH 5.7 and low ionic strength ($<0.3$) has been found. A disulfide bond between fibrinogen molecules in cold-insoluble fibrinogen fraction has been demonstrated. It has been thought that the cold-insoluble precipitate that formed from normal plasma was a reaction between cold-insoluble globulin (CIg), fibrinogen and fibrin.

The plasma proteins can be separately isolated by: 1) organic solvents such as methanol or ethanol at low temperature using Cohn's fractionation, 2) cryoprecipitation, 3) chemical precipitation of plasma with salts such as ammonium sulfate, potassium phosphate, and sodium citrate, and 4) other methods. The solubility of the plasma proteins in these substances decreases in the order of albumin, globulin, and fibrinogen. The latter precipitates first and albumin last upon the addition of increasing amount of the precipitating agent.

1. Ethanol Fractionation (Cohn's fractionation)

In this process, 1,000 to 1,500 liters of 4,000-6,000 human source plasma are pooled and treated sequentially in the cold with various concentrations of ethanol and buffers to precipitate fractions containing different plasma proteins. Fibrinogen is the first material precipitated and harvested at $-5°$ C. with 25% ethanol at a pH of 6.9. Variables determining the precipitation of proteins are ethanol concentration, pH, temperature, ionic strength and protein concentration.

2. Cryoprecipitation

The standard cryoprecipitation method has been primarily used to prepare antihemophilic factor (Factor VIII). Cryoprecipitate also has been known as a source of fibrinogen. The cryoprecipitate method can be also used to prepare fibrinogen concentrate. It is known that some factors might affect the yield of Factor VIII, such as ABO blood grouping, freezing and thawing conditions (see Kasper, et al., "Determinants of Factor VIII Recovery in Cryoprecipitate", Transfusion 15, 312-322, 1975, and Rock, et al., "Variations in Cryoprecipitate Production", Transfusion 17, 50-53, 1977). With respect to Factor VIII preparation, others have studied freezing and thawing conditions (see Brown, et al., "Antihaemophilic Globulin: Preparation by an Improved Cryoprecipitation Method and Clinical Use", Br Med J 2, 79-85, 1967). However, all the factors for cryoprecipitation are not known.

It has been observed that when frozen plasma is thawed in the cold at 4° C., most of the Factor VIII remains in the cold-insoluble precipitate. This precipitate also contains variable amounts of fibrinogen ranging from 100 to 300 mg/single donor unit of cryoprecipitate. It has become routine to prepare anti-hemophilic factor (Factor VIII) and fibrinogen using the cryoprecipitation method in the blood bank using a closed system of plastic bags to maintain the sterility of the product from collection of the whole blood from the donor. See, e.g.: Rousou, et al., "Fibrin Glue: An Effective Hemostatic Agent for Nonsuturable Intraoperative Bleeding", Ann Thorac Surg. 38, 409-410, 1984; Lupinetti, et al., "Cryoprecipitate-Topical Thrombin Glue", J. Thorac Cardiovasc Surg 90, 502-505, 1985; Ness, et al., "Cryoprecipitate as a Reliable Source of Fibrinogen Replacement", JAMA 241, 1690-1691, 1979; Brown, et al., "Antihaemophilic Globulin: Preparation by an Improved Cryoprecipitation Method and Clinical Use", Br Med J 2, 79-85, 1967; Ness, et al., "Fibrinogen in Cryoprecipitate and Its Relationship to Factor VIII (AHF) Levels", Transfusion 20, 93-96, 1980; Carlebjork, et al., "Freezing of Plasma and Recovery of Factor VIII", Transfusion 26, 159-162; Masure, "Human Factor VIII Prepared by Cryoprecipitation", Vox Sang 16, 1-9, 1969, and; Williams, et al., "A New and Improved Method for the Preparation of Autologous Fibrin Glue and Further Applications.", Exhibit Presentation, 71st Annual Clinical Congress of the American College of Surgeons, 1985.

3. Chemical Precipitation

Human fibrinogen can be precipitated from human plasma by ammonium sulfate, polyethylene glycol, plyvinyl-pyrrolidone, and barium/magnesium sulfate. Entering the closed blood bag system for the addition of chemicals opens the system to the potential for bacterial contamination. Small amounts of fibrinogen concentrate solution (0.5-1.9 ml) can be prepared using these methods, but the side effects and safety due to the chemical substances as well as bacterial contamination opportunities are of great concern.

4. Other Methods

Sporadic reports have mentioned the use of the following methods to prepare purified fibrinogen: chromatography, polyelectrolyte fraction technology, recombinant DNA technology and ion exchange chromatography. See C. Th. Smit Sibinga, et al., "Plasma Fractionation and Blood Transfusion", Martinus Nijhoff Publishers, Northland, 1985.

As mentioned above, several methods have been developed for the isolation of purified fibrinogen. However, these have numerous drawbacks that make them inapplicable in clinical use, such as disease transmission (heat treatment intolerable), bacterial contamination (using open system), chemical toxicity and safety, inadequate product volume, time consumption, and cost. Disease transmission is one of the main concerns and the reason the FDA has not approved the commercially prepared fibrinogen concentrate (Tisseel) for use in this country.

Among the methods described previously, the cryoprecipitation method is the simplest and most economic way to make concentrated fibrinogen. Most U.S. blood banks use cryoprecipitate as the fibrinogen (FBG) source for fibrin glue which contains less FBG (260–2,500 mg/dl) compared to Tisseel (7,000–10,000 mg/dl).

Fibrinogen concentrate can be prepared from random single-donor fresh frozen plasma or autologous plasma in sufficient quantity to meet some surgical demand. According to the Standards of the American Association of Blood Banks, fibrinogen concentrate can be currently stored for up to 5 years at −80° C. or at least 5 days at 4° C. until it is needed. Cryoprecipitate contains Factor VIII and fibrinogen and is used to supply fibrinogen in patients with hypofibrinogemia and also as an alternative source of fibrinogen concentrate for fibrin sealant in the United States.

However, traditional cryoprecipitation suffers from problems including the recovery of only small amounts of fibrinogen having low tensile strength when using single-donor cryoprecipitate to prepare fibrin sealant. Further, the fibrinogen concentrates prepared by traditional cryoprecipitation have a concentration range of 260–2,500 mg/dl. This is not an adequate concentration for applying this product as a tissue sealant over highly vascular areas. High fibrinolytic activity over that area breaks down the fibrin clot very quickly. These concentrates have a tensile strength of around 120 gm/cm$^2$ which is usually not sufficient for surgical applications.

The following patents reflect the state of the art of which applicant is aware insofar as these patents appear germane to the patent process. However, it is respectfully stipulated that none of these patents teach singly nor render obvious when considered in any conceivable combination the nexus of the instant invention as set forth hereinafter.

| INVENTOR | U.S. PAT. NO. | ISSUE DATE |
|---|---|---|
| Anderson, et al. | 3,920,625 | 1975 |
| Garber, et al. | 4,025,618 | 1977 |
| Seufert | 4,141,887 | 1979 |
| Shanbrom | 4,188,318 | 1980 |
| Rose, et al. | 4,627,879 | 1986 |

None of the prior art resolves the longstanding and vexing problem that comes from the inefficient extraction of fibrinogen. Optimization of fibrin or fibrinogen extraction particularly as outlined hereinafter, allows for the autologous provision of fibrin from an individual immediately prior to surgery such that the fibrin is extracted from the patient and the residual blood components are restored to the individual with no discernable adverse effects that would mitigate against a commencement of the operation.

SUMMARY OF THE INVENTION

The instant invention is distinguished over the known prior art in a multiplicity of ways. For one thing, the yields associated with the apparatus and methodology according to the instant invention provide enhanced quantities and higher quality of fibrin which allows certain prior art difficulties to have been obviated.

In its elemental form, a reservoir forms an interior of the device which receives heat transfer fluid therewithin which is isolated from the material to be fractionated by cryoprecipitation such as blood or plasma not only by a pouch within which the blood or plasma resides, but also by a membrane which is interposed between the blood pouch and which depends into the reservoir. Thus, should the pouch have a hairline fracture, upon thawing the blood, and if the blood contaminates areas outside the pouch, the contamination will be localized to the interior of the membrane which is configured for expeditious dislodgement from its situ overlying and depending within the reservoir. Replacement with a fresh membrane free from contamination is a minor procedure. Thus, one attribute of the invention is the means by which it takes into account the likelihood of a pouch having a fracture.

The reservoir includes means for storing preferably two heat transfer fluids and maintaining those fluids at two ideal temperatures, typically one near −30° C., and the other at 3° C. Upon deployment of the pouch of the material to be fractionated within the membrane, the membrane depends within the reservoir and a first, freezing fluid is directed at the membrane in two distinct manners. A first manner involves raising the liquid level of the heat transfer fluid up around the membrane and the fractionable material within the pouch so that hydrostatic pressure exists on the membrane causing it to collapse so that it conforms to the exterior contour of the pouch. The absence of an air gap between the membrane and the pouch assures that the thermal profile in heat exchange is optimal.

A second manner in which the first freezing fluid thermally contacts the pouch takes the form of a pulsation in which exterior surfaces of the membrane pocket receive the freezing fluid from a nozzle such that the freezing fluid impinges on the membrane pocket and indirectly against the pouch, adding a mixing action from the deceleration of the freezing fluid. An ancillary benefit attends this pulsation. As the blood, platelet or plasma within the pouch starts to freeze, the pulsation maximizes the effect of areas of accelerated freezing and crystallization.

After the freezing step, a second heat transfer fluid is caused to coact against the membrane and pouch, this time, however, heating the contents within the pouch from its cold temperature to a thawed temperature, preferably around +3° C. As before, the liquid level of the heat transfer fluid is raised up around the membrane and contacts the fractionable material within the pouch through the membrane so that hydrostatic pressure exists on the membrane causing it to collapse and conform to the exterior of the pouch. In addition, the nozzles are again caused to coact against the membrane and pouch which in this case allows the kinetic energy to be dissipated by contact directly against the membrane and indirectly against the pouch adding a mixing action from the deceleration of the thawing fluid thereagainst. As before, this type of pulsation serves to knead the contents within the pouch, forcing circulation therewithin and therefore accelerating the thawing process. Ultimately, the center of the thermolabile, transfusible fluid within the pouch will have been thawed prior to the outer periphery especially because there has been pulsing on two major faces of the pouch.

In a preferred form of the invention, two such nozzles are provided one on each side of the pouch and are synchronized to contact the pouch simultaneously, so that equal and opposite forces are experienced on both sides of the pouch, providing forced circulation of the fractionable material as it changes phase. This synchronous pulsing also keeps the pouch stable and free from oscillation.

Another benefit of the forced circulation of both the freezing and thawing fluid within the pouch is that it occurs in a substantially toroidal manner so that there is internal circulation which is simulative of the kneading. By attacking the geometrical center of the bag through the pulsing liquid, the fractionating process will have been accelerated.

Other types of kneading could occur by either different orientation of nozzles in their contacting relationship with the pouch or by other means by which the pouch is manipulated. For example, variously shaped platens can move in jaw-like concert to intermittently squeeze the bag. Other forms of vibratory excitation could also provide the similar benefit.

As the result of the above-described structure and methodology, fluids such as blood, platelets or plasma or even pharmaceutical products can be fractionated and then centrifuged for separation by decanting. Typically less than 6 minutes is required for 250 ml. of plasma to be taken through one change of phase.

OBJECTS OF THE INVENTION

Accordingly, it is a primary object of the present invention to provide a novel and useful device and method for rapidly freezing and thawing fractionable material such as blood, platelets or plasma followed by centrifuging and then decanting for subsequent use, such as in an operation.

A further object of the present invention is to provide a device as characterized above which minimizes the likelihood of contamination should a pouch containing the fractionable material have a fracture therewithin which would be most easily discernible only upon thawing of a once frozen pouch. In the event that such a fracture occurs, a primary object of the present invention is to reinitialize the apparatus of the present invention expeditiously and with minimal downtime caused by the contamination.

A further object of the present invention is to provide a device as characterized above which minimizes the existence of unwanted thermal gradients which may delay the formation of the product when fractionating.

A further object of the present invention is to provide a device as characterized above which benefits from a pulsation coacting against the pouch containing the fractionating material to provide improved circulation thereby accelerating the separation process.

A further object of the present invention is to provide a device as characterized above which does not require the attention of personnel and therefore allows the separating process to be performed with substantially minimal attention.

A further object of the present invention is to provide a device as characterized above which is automated and regulated such that the fractionating process, while unattended provides uniform results.

A further object of the present invention is to provide a device as characterized above which lends itself to mass production techniques, is safe and easy to use, and is extremely durable in construction.

A further object of the present invention is to provide a device as characterized above which substantially shortens the amount of time required for phase change of fractionable fluids contained in pouches especially in emergency situations or involving the requirement of blood for lifesaving situations.

A further object of the present invention is to achieve a method of isolating fibrinogen which can be carried out in blood banks, which follow the Standards of American Association of Blood Banks for preparation conditions in a closed bag system, and which also produces a high yield of fibrinogen capable of producing a clot of high tensile strength.

An additional object is to produce a fibrinogen concentrate for use in fibrin glue and the like, which has increased fibrinogen concentration and increased tensile strength.

Another object is to obtain a fibrinogen concentrate which overcomes the disadvantages of the known prior art.

In accordance with the present invention, fibrinogen concentrate is prepared by a cryoprecipitation method which employs at least two freeze-thaw cycles. A cryoprecipitation method according to the present invention concentrates fibrinogen by the steps of: subjecting fractional material to a freeze-thaw cycle by freezing the fractionable material, and then thawing the frozen fractionable material, subjecting the fractionable material to a second freeze-thaw cycle by freezing and then thawing the frozen plasma and then centrifuging the fractionable material to concentrate cryoprecipitated fibrinogen; and separating the fibrinogen from the remainder of the fractionable material. The fractionable material could be whole blood, plasma or platelets.

A fibrinogen product prepared in accordance with this invention advantageously has a higher concentration and increased volume of fibrinogen (about 4,000-6,000 mg/dl FBG in 3-5 ml) than achieved by conventional cryoprecipitation methods. According to the present cryoprecipitation process, a fibrinogen product can be readily prepared having from about 2-6 times more fibrinogen than the standard cryoprecipitation method.

Viewed from one vantage point, it is an object of the present invention to provide a device for transferring heat with respect to a fractionable product which is stored in a flexible pouch to cryofractionate the product, comprising a housing, suspension means in said housing for receiving the pouch and holding the pouch such that major surface areas of the pouch are accessible, heat transfer means oriented to address the major surfaces of the pouch including at least one heat transfer fluid such that upon contact with said one heat transfer fluid, the fractionable product within the pouch approaches the temperature of the heat transfer fluid, and means for circulating the product in the pouch to minimize thermal gradients within the pouch during heat transfer.

Viewed from a second vantage point, it is an object of the present invention to provide a device for cyclically transferring heat between an article at one temperature and a fluid maintained at another temperature and back again which includes a membrane interposed between the fluid and the article, the membrane isolating the fluid from the article such that the fluid contact with the article is indirect and temperature change passes through the membrane, and means for pulsing the fluid is provided oriented to impinge the article through the membrane, whereby the fluid pulsing means induces thermal circulation into the article for better heat transfer.

Viewed from a third vantage point, it is an object of the present invention to provide a device for rapidly and cyclically freezing and thawing fractionable materials such as blood or plasma for use in an operation as needed which comprises a reservoir adapted to receive heat transfer fluid therewithin and isolated from the fractionable material by a membrane, the membrane interposed between the fractionable material and the reservoir to preclude contact with the heat transfer fluid, and pulsing means to deliver the heat transfer fluid against the fractionable material by pulsing passing through the membrane, the pulsing means and the heat transfer fluid collectively defining a massaging means against the fractionable material to promulgate rapid phase change of the fractionable material by circulating the fractionable material for better heat transfer.

Viewed from a fourth vantage point, it is an object of the present invention to provide a method for rapidly changing phase of fractionable fluid from a liquid state to a frozen state and back again, the steps including pulsing thermal fluid against a pouch containing the fractionable fluid to change the temperature of the fractionable fluid and circulate the fractionable fluid within the pouch as it changes phase and maintaining the thermal fluid at a temperature different from the temperature of the fractionable fluid to allow the fractionable fluid to approach the thermal fluid.

These and other objects will be made manifest when considering the following detailed specification when taken in conjunction with the appended drawing figures.

DESCRIPTION OF PREFERRED EMBODIMENTS

Referring to the drawings now, wherein like reference numerals refer to like parts throughout the various drawing figures, reference numeral 10 is directed to the device for fractionating constituent components from a material using cryoprecipitation according to the present invention.

In essence, the device 10 is formed from a housing 30 having a control panel 12 on one exposed surface thereof and an opening 40a on a top wall 16 and within which a flexible membrane 50 is provided. The membrane 50 occludes an interior 70 of the housing 30 from an exterior. The membrane 50 is removably inserted to depend within the interior 70 so that a pouch P can be removably inserted into the membrane 50 and therefore into the interior 70. The pouch P is then exposed to heat exchange fluid F and fluid pulsation through the membrane 50.

Figure 1:
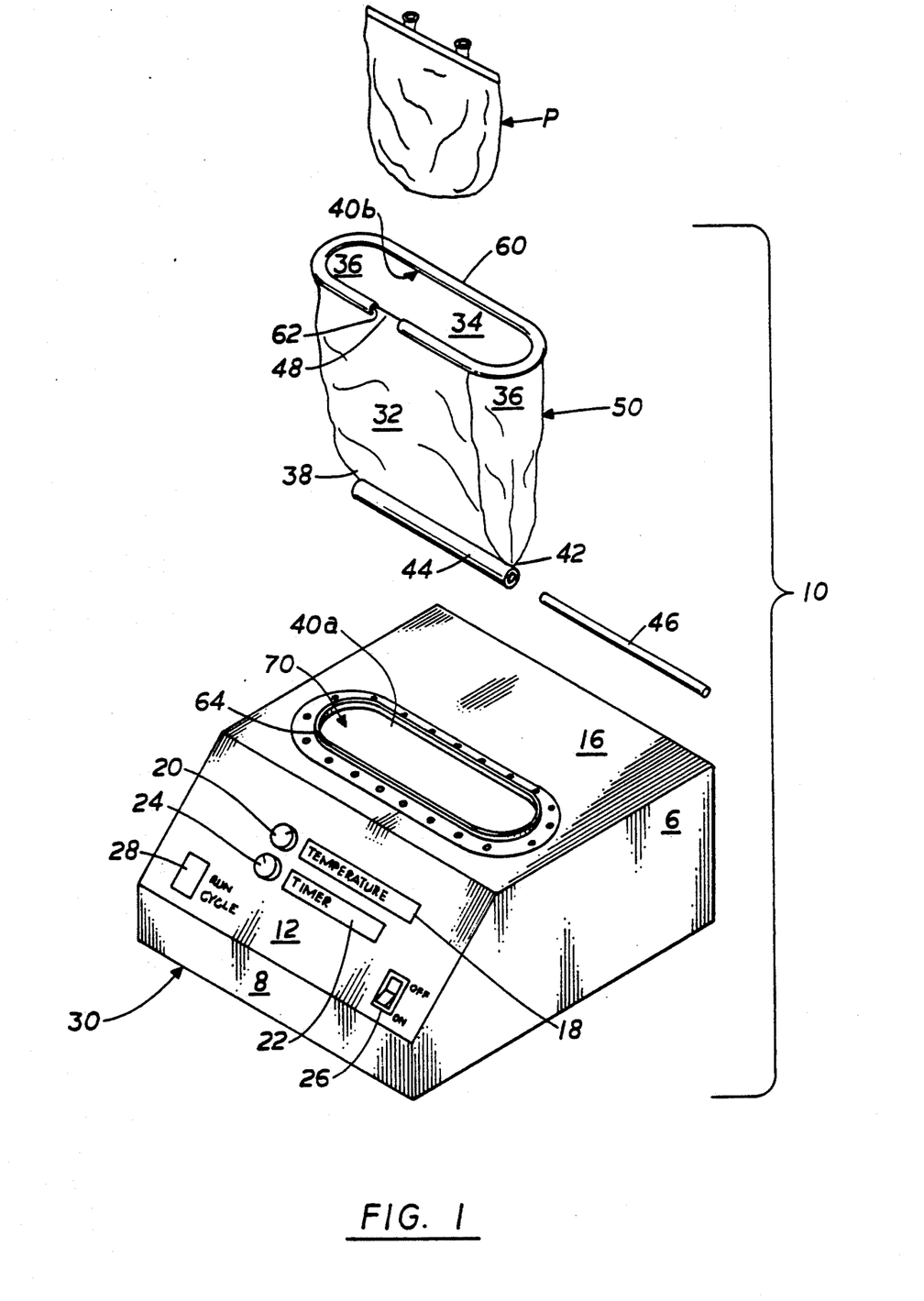
FIG. 1 is a perspctive view, showing exploded parts of the apparatus according to the present invention.
Figure 2:
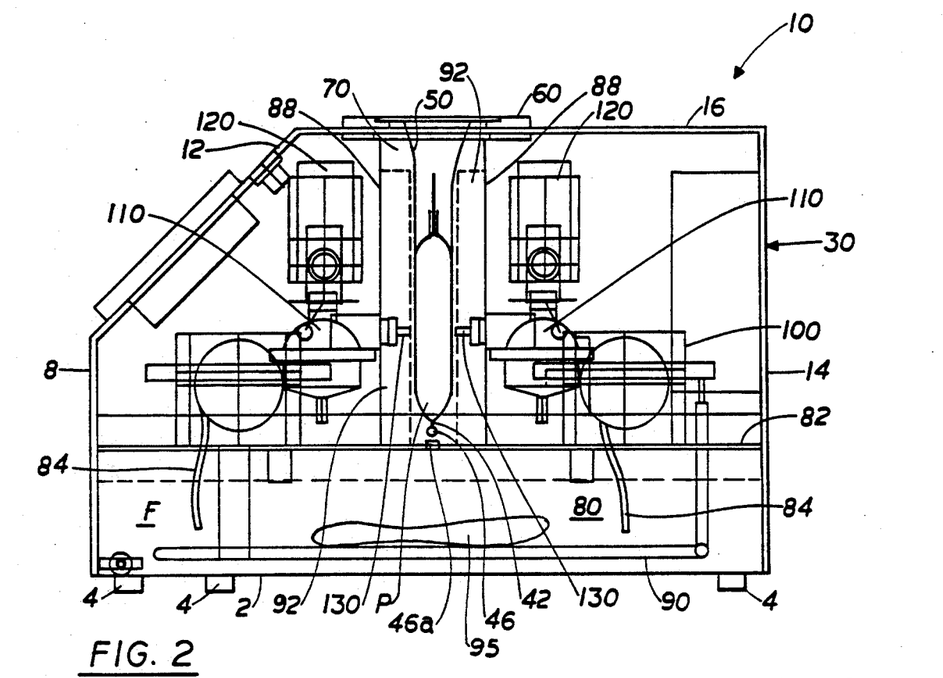
FIG. 2 is a transverse longitudinal sectional view of the apparatus according to the present invention showing a loading or removing cycle.
Figure 3:
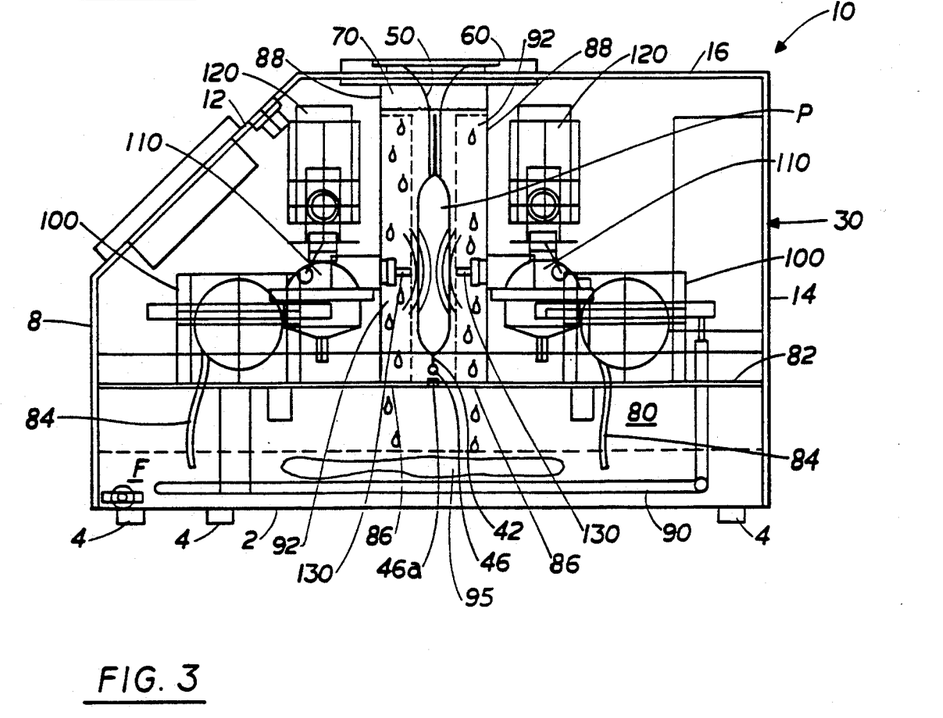
FIG. 3 is a view similar to FIG. 2 schematically showing the device in operation.
Figure 4:
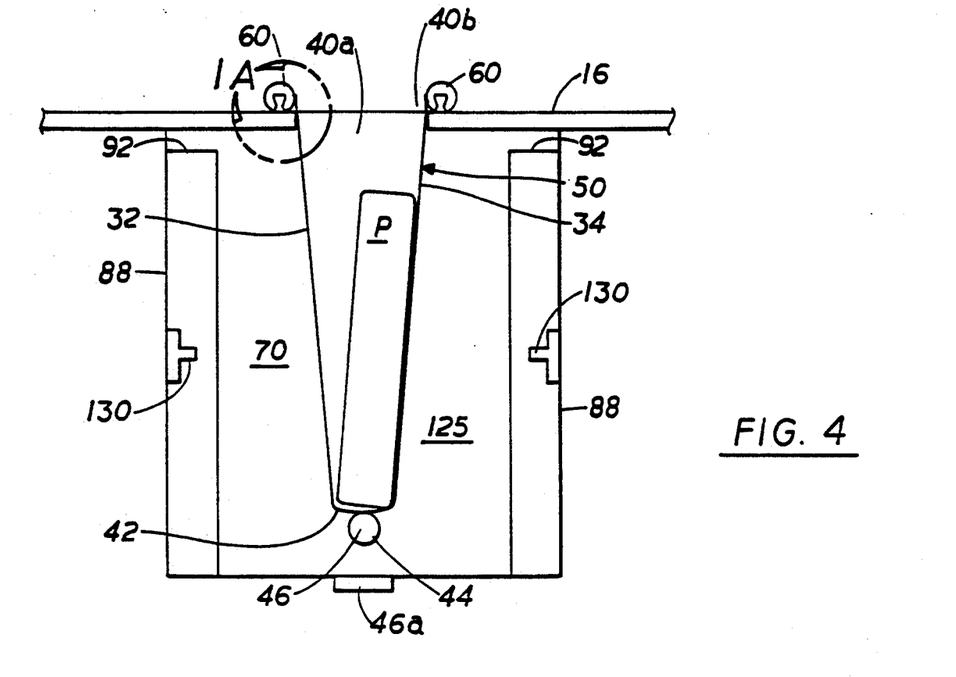
FIG. 4 is a detail of a portion of the FIG. 2 structure.
Figure 5:
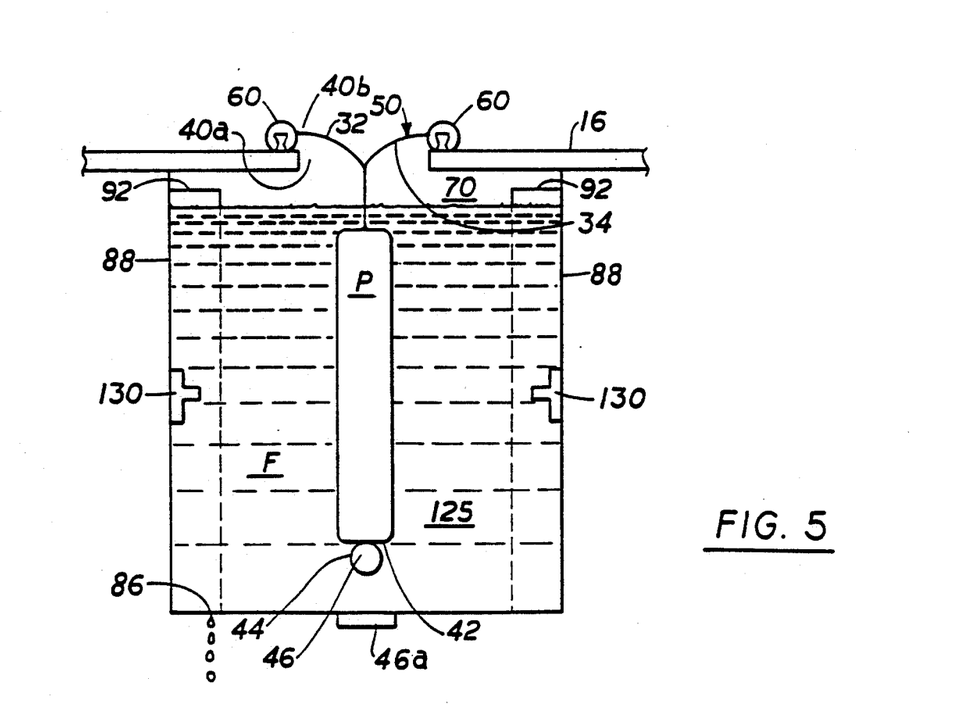
FIG. 5 is a detail of a portion of the FIG. 3 structure.

More specifically, the housing 30 from a side view is a substantially rectangular construct having one corner of the rectangular construct truncated or mitered providing an inclined surface upon which a control panel 12 is provided. With reference to FIGS. 1 through 3, the housing 30 includes a bottom wall 2 supported on a surface by means of feet 4 disposed on a bottom surface of wall 2. The bottom wall 2 is preferably substantially rectangular in configuration and planar and has two parallel side edges from which extend two vertical side walls 6 one each on opposed side edge extremities. In addition, a front wall 8 extends up from a front edge of the bottom wall 2. A rear wall 14 extends up from a rear edge of the bottom wall 2 which is parallel to the front wall edge. A top wall 16 is provided which joins the side walls 6 and rear wall 14. Had the front wall 8 been similarly joined with the top wall 16, an orthorhombic rectangular construct would have been provided. Instead, an inclined control panel wall 12 extends from a top edge of the front wall 8 to a forward edge of the top wall 16. Thus, to accommodate the control panel 12, the side walls 6 are truncated at corners adjacent the control panel 12 to complete the housing 30.

The control panel 12 supports a temperature indicator 18 used to indicate the temperature of the heat exchange fluid F in a manner to be described. In addition, a temperature control 20 allows alteration of the temperature of the heat exchange fluid F as reflected by the temperature indicator 18. The control panel 12 also supports a timer 22 indicating the amount of time that the heat exchange fluid F will circulate (in a manner to be described) and a timer control 24 is provided on the panel 12 to alter the amount of time that will define one cycle for the heat exchange processes. If desired, a commercially available digital touch pad could be used for not only the timer and its control but also for the temperature and its control. An on/off switch 26 is operatively coupled to provide power to the device 10 and is also supported on the control panel 12. An indicator 28 is also provided on the control panel 12 and indicates whether or not the device 10 is in the midst of a cycle for fractionating material by cryprecipitation. The indicator 28 may be in the form of a pilot light and/or may include an audible alarm.

As mentioned briefly, the housing 30 includes an opening 40a through which a membrane 50 is provided which occludes the interior 70 defined by the housing walls 2, 8, 12, 16 discussed hereinabove. In essence, the membrane 50 is sufficiently flexible to receive a fractionable thermolabile product such as a pouch P of blood, plasma or platelets therewithin so that it can be cryoprecipitated expeditiously. The membrane 50 is formed from a front panel 32, a rear panel 34, two side panels 36 and a bottom panel 38. The two side panels 36 and bottom panel 38 connect the front and rear panels 32, 34 together respectively at side and bottom edges of the front and rear panels 32, 34 so that an enclosure is provided having an upper opening 40b which is substantially complemental to the opening 40a of the housing 30.

In addition, the membrane 50 preferably includes a skirt 42 of material depending from the bottom panel 38. The skirt 42 has a sleeve 44 at a lowermost extremity of substantially cylindrical configuration and substantially coextensive with the width of both the front and rear panels 32, 34. A hold-down rod 46 is inserted within the sleeve 44 and is used as anchor to offset the effects of buoyancy associated with the heat transfer fluid F to be described hereinafter. The hold-down rod 46 may have a magnetic component which cooperates with another magnet 46a, located on a top surface of a shelf 82 to offset buoyancy. Another version may embody the rod 46 as substantially U-shaped with legs extending upwardly, parallel to the side panels 36.

Figure 1A:
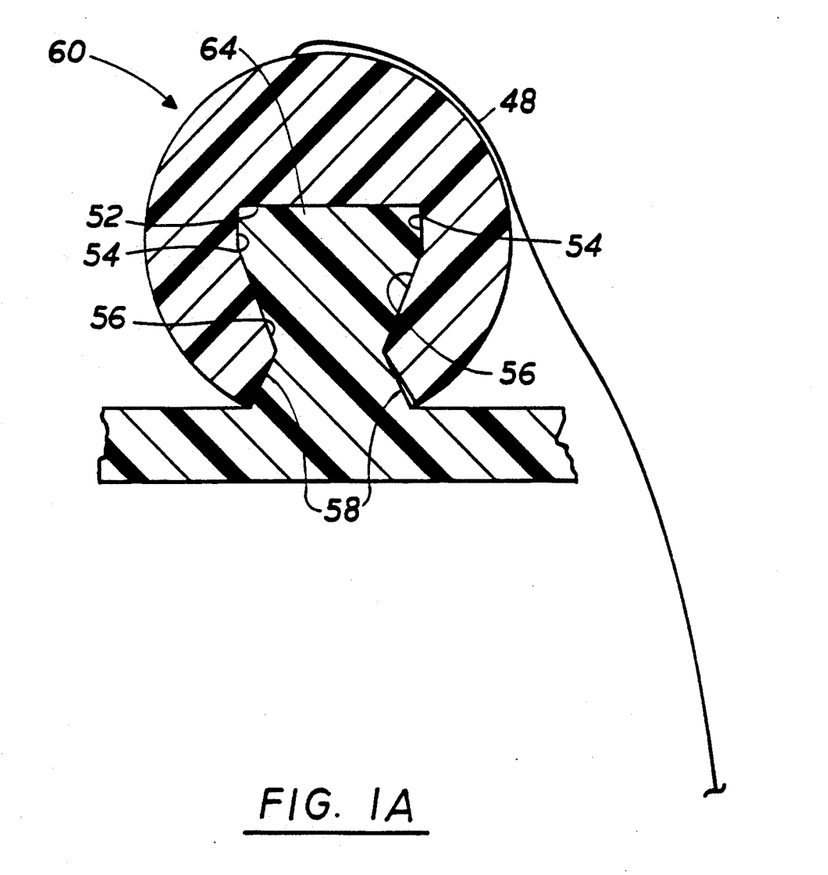
FIG. 1A is directed to a detail of FIG. 4 along lines 1A—1A in section.

The topmost portion of the membrane 50 adjacent the opening 40b includes a peripheral flange 48 defining a turnout of the membrane 50. This flange 48 supports a snap-on coupling 60 having an oval configuration which is somewhat complemental to the opening 40b of the flexible membrane 50. The coupling 60 also circumscribes the opening 40a of the housing 30. Coupling 60 can suspend beneath flange 48 or be integrally formed therewith or be bonded thereto. The snap-on coupling 60 has an outer profile of substantially circular configuration, shown best in FIG. 1A, with an opening 62 to define an interior therewithin defining a retention mechanism which adheres to a ridge 64 on the top wall 16 of housing 30.

More specifically, the interior of the coupling 60 is formed from a pair of spaced guide channels 58 which diverge outwardly and which lead to retention channels 56 which diverge inwardly. Two parallel, facing support channels 54 communicate with the retention channels 56 and terminate in an abutment channel 52 which rests on a top surface of ridge 64 that circumscribes the outer periphery of the housing opening 40a. Thus, whereas the coupling 60 defines a recess, the ridge 64 defines a projection with a contour complemental to the snap-on channel 60 for frictional retention therebetween.

The construction thus far enumerated with respect to the snap-on channel 60 and ridge 64 lend themselves to the expeditious removal of the flexible membrane 50 should it become contaminated when a pouch of fractionable thermolabile fluid (such as blood) becomes fractured before or during the cryoprecipitating process and contaminates the interior of the flexible membrane 50. Thus, the ridge 64 defines a male projection complemental to the recess integrally formed on the snap-on coupling 60 and allows rapid replacement.

Attention is now directed to FIGS. 2 and 3 with respect to the operation mechanism by which a pouch P of fractionable material can be inserted into the membrane 50 located within the interior 70 of the device 10 and rapidly cycled between optimal temperatures for cryoprecipitation and then for other subsequent purposes. It is to be noted that the membrane 50 is characterized as one which is extremely flexible and yields to hydrostatic pressure induced by the presence of the heat transfer fluid F on an outside surface thereof so that the pouch P (when placed within the interior of the membrane 50) will have the membrane 50 collapse around the pouch P and conform to the configuration of the pouch P with no air gaps for optimal heat transfer. One suitable material for this membrane 50 is polyetherurethane, although other thin hydrostatically flexible material such as Teflon ® would be serviceable.

Comparison between FIGS. 2 and 3 shows the membrane 50 collapsing around the pouch P and conforming to the pouch P in the presence of hydrostatic pressure. More specifically, a sump 80 is provided at a lowermost portion of the device 10 and collects the heat transfer fluid F therewith. Typically, a silicone heat transfer fluid F would be adequate to operate within the contemplated temperature range of typically −30° C. to +37° C. The sump 80 holds the heat transfer fluid F therewithin. An immersion heater 90 elevates the heat transfer fluid F to a substantially constant temperature. Typically the target temperature of the pouch P when heated is 4° C. As mentioned earlier, the temperature of the fluid F can be controlled on the control panel 12 by an appropriate mechanism.

A cooling element 95 is also located in the sump 80 and is operatively coupled to a source of power and the temperature/timer controls 18, 20, 22, 24. This cooling element 95 can maintain the heat transfer fluid F at and below the freezing point of the fractionable material. For blood products, −30° C. is adequate.

A pump 100 is placed above the sump 80 and supported on an intermediate platform 82 supported in the housing 30. The pump 100 includes an inlet 84 which extends into the heat transfer fluid F contained in the sump 80. The inlet 84 delivers the heat transfer fluid F to the pump 100 so that it can be administered on an exterior surface of the membrane 50 (i.e. on a surface of the membrane 50 opposite from that surface of the membrane 50 contacting the pouch P) following the preferred manner. The pump 100 administers heat transfer fluid F to a geometrical center of the pouch P ("through" the membrane 50) by means of a nozzle jet 130. By geometrical center it is meant the surfaces of the pouch P remote from side edges thereof which define a periphery. By the jet 130 impinging on the pouch P along major surfaces thereof and preferably at the geometrical center of the pouch P, the core of the fractionable fluid contained within the pouch P will be rapidly thawed or cooled and effectively circulated in the following manner.

It is preferred that the nozzle jet 130 pulse heat transfer fluid F at the geometrical center of the membrane 50 and pouch P. In order to achieve same, the nozzle 130 has interposed between its outlet and the pump 100 a solenoid valve 120 and a surge chamber 110. The surge chamber 110 is closer to the pump 100 than the solenoid valve 120. In use and operation, as the pump 100 provides continuous fluidic pressure by delivering heat transfer fluid F from the sump 80 through the pump 100 and to a surge chamber 110. Cyclic opening and closing of the solenoid valve 120 provides pulses from the nozzle jet 130 hitting the geometrical center of the pouch P.

The surge chamber 110 is configured in such a manner that increasing fluidic pressure exerted by the pump 100 will be stored as potential energy in the surge chamber 110 whereupon, by opening of the solenoid valve 120, the potential energy within the surge chamber 110 converts immediately to kinetic energy and vents outwardly through the nozzle jet 130. The nozzle jet 130 may have appropriate nozzle geometry such as converging, diverging throat areas to achieve acceleration at its outlet and an appropriate "needle" or "spray" pattern.

In a preferred form of the invention, a pair of nozzles 130, one each disposed on opposite major surfaces of the membrane 50 and therefore the pouch P are provided. One way to achieve two nozzles 130 operating in concert would be to have a solitary pump 100 delivering heat transfer fluid F to both of the nozzles 130 with a manifold delivering to the nozzle jets 130 simultaneously. It is preferred that each nozzle 130 administer a pulse of heat transfer fluid F to the geometrical center of the membrane 50 at the same time, to preclude oscillation or rocking of the membrane 50 back and forth. However, a branch manifold such as just described may provide an unwanted reduction in pressure of the nozzle 130 output. In such an event, a pair of pumps 100 (shown in the drawing FIGS. 2, 3 and 7) along with a pair of surge chambers 110 and solenoid valves 120 are provided, with the firing of the solenoid valves 120 synchronized with electrical means (not shown) to achieve simultaneous firing of the nozzles 130.

It should be noted that multiple jets or jets 130 oriented off-axis from the geometrical center can impart other types of internal kneading of the contents in pouch P when strategically fired. When the jets 130 are staggered and/or fired sequentially, rotary motion or different types of mixing can be effected.

Also vertical oscillatory motion can also be imparted by intermittent actuation of the magnetic pair 46, 46a shown in FIG. 2. Magnet pairs could be located elsewhere within chamber 125, (for example one on the partition 88 and another elsewhere on the membrane 50), to induce other types of motion, as should now be evident. Collectively, the jets 130 and magnets 46, 46a can induce complex motion by operating in concert.

FIG. 3 reflects another preferred scenario for the most expeditious heat transfer of the contents within the pouch P. It is contemplated that the rate at which the heat transfer fluid F contacts the membrane 50 and pouch P is greater than the ability of the heat transfer fluid F to be drained from a weep hole 86 placed through the platform 82 and thence to the sump 80. The distribution of the heat transfer fluid F by means of the nozzles 130 will thus cause accumulation of the heat transfer fluid F within a chamber 125 circumscribing the membrane 50 and defined by partitions 88 (located forward and rearward of the membrane 50) and the side walls 6. Partitions 88 allow the liquid level of heat transfer fluid F to rise to ensconce the membrane 50 and cause the membrane 50 to collapse upon the pouch P by hydrostatic pressure. Even with the presence of heat transfer fluid F within this chamber 125, the nozzle jets 130 are configured to still provide pulsing shocks through the heat transfer fluid F and to the membrane 50 and therefore the pouch P. At least one spillway 92 encourages the heat transfer fluid F, once it has risen to the level of the spillway 92, to re-enter the sump 80 to maintain the temperature of the heat transfer fluid F substantially constant at a target temperature. Note that the weep hole 86 is preferred to communicate with the spillway 92. This beneficially controls the rate at which heat transfer fluid F seeps from the chamber 125.

Figure 6A:
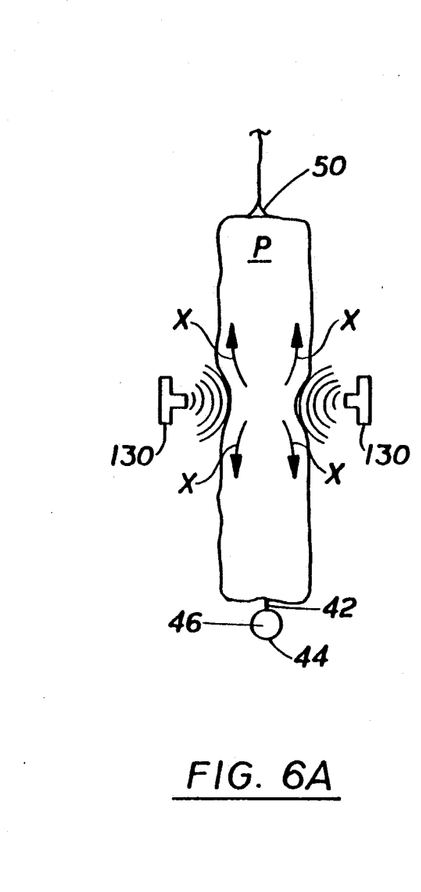
FIGS. 6A, 6B, 6C and 6D explain the phenomena of the pulsation and internal circulation according to the instant invention.
Figure 6B:
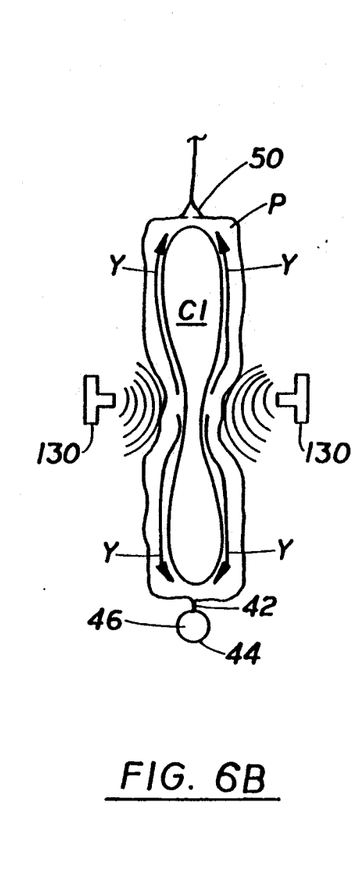
Figure 6C:
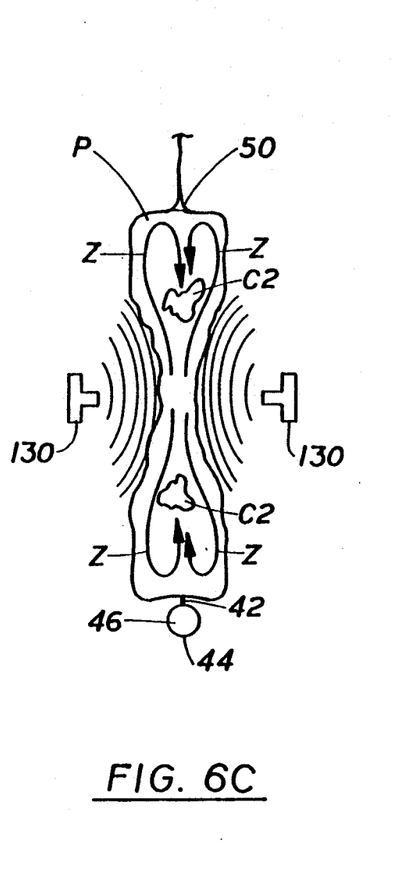
Figure 6D:
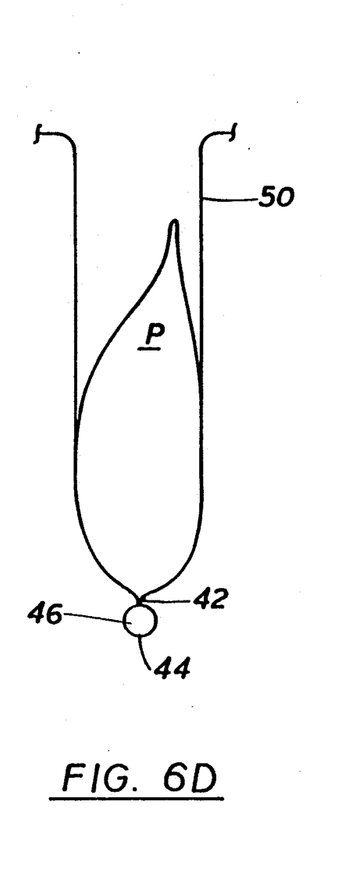

FIGS. 6A through 6D reflect the various stages in the freeze-thaw cycle for a pouch P of thermolabile, fractionable material. FIG. 6D reflects fractionable material in a pouch P which is not frozen. FIG. 6A reveals a frozen pouch P. FIG. 6A also reflects the scenario when the membrane 50 has already been ensconced in heat transfer fluid F and has constricted around the pouch P and the nozzle jets 130 are continuing to work on the pouch P through the membrane 50. As shown therefore, in FIG. 6A, the pouch P and membrane 50 have a somewhat rectangular configuration or the exact configuration of the frozen pouch P. The initial thermal pulsing causes a minor indentation at the area of impingement with the nozzle jets 130 and liquid thawed from the pouch P is starting to circulate, as shown by arrows X, between the skin of the pouch P and the frozen fractionable cryoprecipitate material. In FIG. 6B there has been sufficient melting at the core of the pouch P to encourage greater fluid circulation of the fractionable cryoprecitable material such as shown by the arrows Y and when contrasted with the arrows X of FIG. 6A. There is still, however, a core of material $C_1$ which is substantially shaped like a FIG. "8" in cross-section but the outer fluid is becoming thicker, working and diminishing the size of the frozen core $C_1$. FIG. 6C shows the scenario where only a minor frozen core $C_2$ exists and the fluid migration forces Z are pushing the frozen core $C_2$ closer to the pulsating center. Finally, FIG. 6D shows the pouch P when it is completely thawed and in a flaccid state.

With the foregoing structure in mind, the following methodology for its utilization should now be more evident. A pouch P of material containing blood, plasma, platelets or the like is initially introduced into the device 10 by placement into the opening 40b of the membrane 50 to achieve a substantially FIG. 6D configuration. With the device turned on, the working heat transfer fluid F collapses the membrane 50 upon the pouch P by raising the liquid level within the chamber 125. Concurrently, the nozzles 130 pulse liquid towards the pouch, through the membrane 50. Because of the internal circulation attending this chilling process, a frozen core, similar to $C_2$ will occur. As the temperature continues to decrease, the core will enlarge such as shown at $C_1$ in FIG. 6B and will ultimately solidify. It is desired that the temperature when totally frozen be somewhere between 0° C. and −30° C. Thereafter, the process reverses using a heat transfer fluid F which proceeds to melt the contents of the pouch P as in the sequence described with respect to FIGS. 6A through 6C hereinabove.

Figure 7:
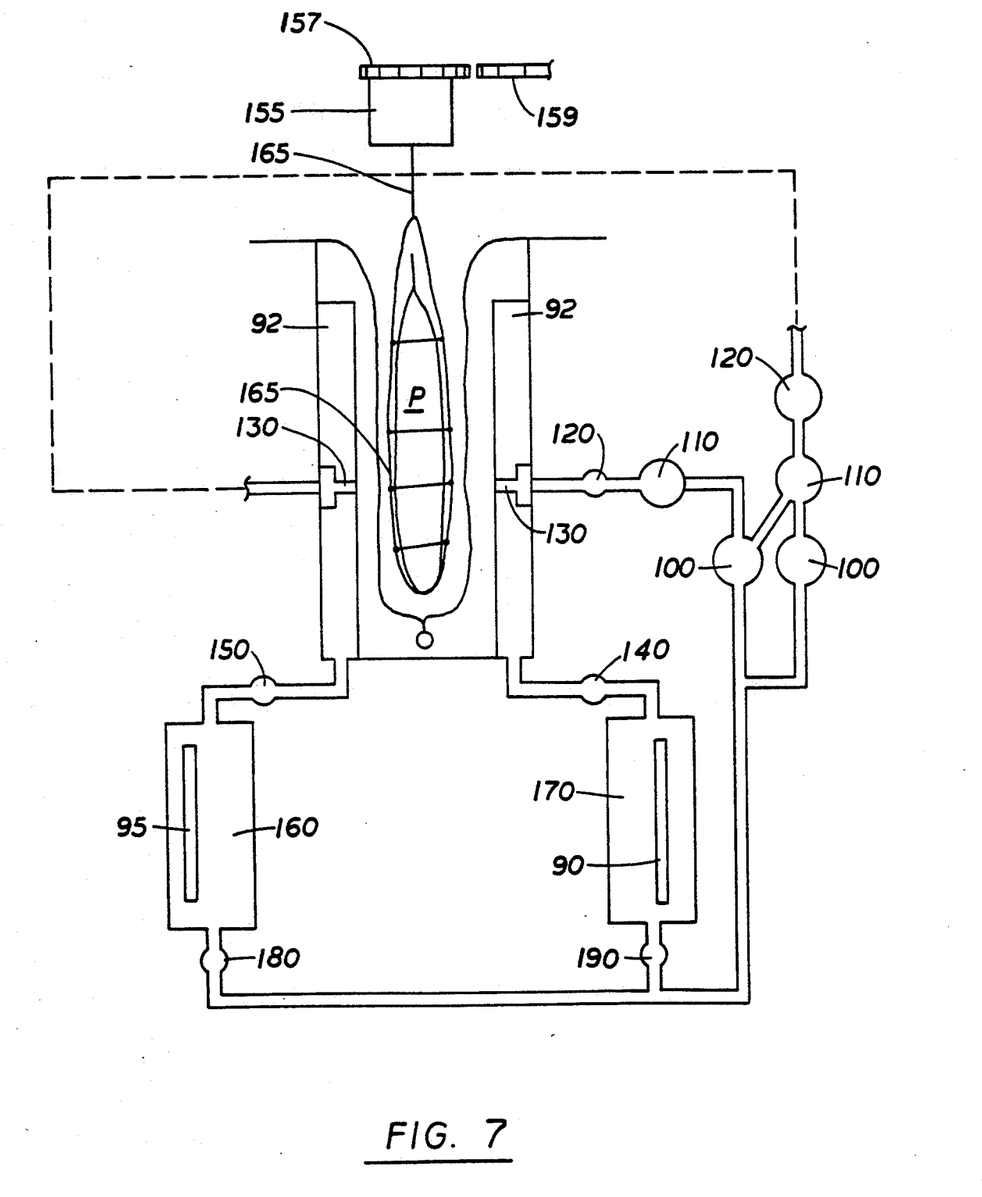
FIG. 7 shows a fluid flow schematic.

Whereas FIGS. 2 and 3 reflect one scenario for heating and cooling heat transfer fluid F contained within a single sump 80, FIG. 7 reflects the realization that for the most rapid cycling, it is more efficient to have separate tanks for the coldest fluid F and hottest fluid F so that there is no downtime in cycling from the freezing process to the heating process consecutively.

As shown in FIG. 7, therefore, two stand pipes 92 are provided one of which is for heating of the heat transfer fluid F which is directed through a valve 140 into a tank 170 within which the heating element 90 is operatively connected. During the heating process, therefore, valve 140 and valve 190 are open allowing the heat transfer fluid F to circulate to the pumps 100 and therebeyond. The valve 180 remains closed isolating the cooling heat transfer fluid F.

Another stand pipe 92 is directed through a valve 150 into a tank 160 within which cooling element 95 is operatively connected.

During the freezing process, therefore, valve 140 is kept open allowing heat transfer fluid F to drain through the stand pipe 92 and into the tank 170. Valve 190 is closed. Valve 180 is opened allowing the circulation of the freezing fluid F to the pump 100 and nozzles 130 therebeyond. Both valves 140 and 150 can be remotely operated as by a solenoid. With the valve 150 and valve 180 closed, the cooling element 95 operatively coupled to a source of power allows the heat transfer fluid F contained within the storage tank 160 to be maintained at an optimal temperature. Typically, this temperature is near −30° C. In any event, the liquid contained in the tank 160 is allowed to be pumped through pump 100 by an open valve 180 and a closed valve 190. In this way, the working heat transfer fluid F does not have to go through the extremes of temperature during each cycle. Also shown in FIG. 7 is the structure mentioned hereinabove where one or two pumps could be used and if one pump were to be used a separate branch for the surge valves 110 and firing solenoid valves 120 are provided.

Also in FIG. 7, another means for massaging the pouch P is suggested. More specifically, a solenoid 155 is operatively coupled to reciprocate a rod and pouch holder 165, which when the pouch P has been grasped by hydrostatic pressure through the membrane 50 will induce circulation within the pouch P. A gear mechanism 157, 159, prehaps coupled to the solenoid holder rod assembly can impart twisting to the pouch P.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A device for cyclically transferring heat between an article at a first temperature and a fluid maintained at a second temperature and then returning the heat thus transferred back again, comprising, in combination:
   a membrane interposed between said fluid and the article, said membrane isolating said fluid from the article such that fluid contact with the article is indirect and heat transfer occurs through the membrane,
   and means for pulsing said fluid oriented to impinge the article through the membrane,
   said fluid pulsing means inducing circulation within the article for better heat transfer; and
   wherein two sumps are provided with valve means so that said fluid can be stored in both of said sumps, and
   one said sump includes a heating means for heating said fluid therein,
   said other sump includes cooling means for cooling said fluid therein,
   and said valve means cycles between said two sumps for cyclical heating and cooling;
   whereby heat transfer may oscillate from being directed into the article to being directed out of the article.

2. The device of claim 1 wherein said membrane includes means for rapid replacement of said membrane within said device should the article placed within said membrane for heat transfer be fractured and expose its contents to said membrane; and
   wherein said fluid is incompressible.

3. The device of claim 1 wherein said pulsing means includes a plurality of nozzles oriented to impinge directly on said membrane and therefore indirectly on the article such that kinetic energy of said fluid is dissipated by contact against the membrane directly and indirectly on the article.

4. The device of claim 3 wherein two said pulsing nozzles are provided on diametrically opposed sides of said membrane and the article.

5. The device of claim 4 wherein said two nozzles include means to synchronize and operate in concert such that each said nozzle emits a quantum of fluid at the same instant, and said nozzles are equally distant from said membrane for simultaneous contact on said membrane.

6. The device of claim 1 wherein said membrane is oriented within a compartment which allows fluid build-up against said membrane and said compartment includes a spillway oriented above the pouch which facilitates recirculation of the fluid from the compartment to an underlying sump.

7. The device of claim 6 wherein said compartment includes a weep hole drain means to return the fluid back to said sump in addition to said spillway.

8. A device for cyclically transferring heat between an article at a first temperature and a fluid maintained at a second temperature and then returning the heat thus transferred back again, comprising, in combination:
   a membrane interposed between said fluid and the article, said membrane isolating said fluid from the article such that fluid contact with the article is indirect and heat transfer occurs through the membrane,
   and means for pulsing said fluid oriented to impinge the article through the membrane,
   said fluid pulsing means inducing circulation within the article for better heat transfer;
   wherein said membrane includes means for rapid replacement of said membrane within said device should the article placed within said membrane for heat transfer be fractured and expose its contents to said membrane;
   wherein said pulsing means includes a plurality of nozzles oriented to impinge directly on said membrane and therefore indirectly on the article such that kinetic energy of said fluid is dissipated by contact against the membrane directly and indirectly on the article;
   wherein two said pulsing nozzles are provided on diametrically opposed sides of said membrane and the article;
   wherein said two nozzles include means to synchronize and operate in concert such that each said nozzle emits a quantum of fluid at the same instant, and said nozzles are equally distant from said membrane for simultaneous contact on said membrane;
   wherein said membrane is oriented within a compartment which allows fluid build-up against said membrane and said compartment includes a spillway oriented above the pouch which facilitates recirculation of the fluid from the compartment to an underlying sump;
   wherein said compartment includes a weep hole drain means to return the fluid back to said sump in addition to said spillway; and
   wherein two sumps, two spillways and two weep holes are provided with valve means so that said fluid can be stored in both of said sumps, and
   one said sump includes a heating means for heating said fluid therein,
   said other sump includes cooling means for cooling said fluid therein,
   and said valve means cycles between said two sumps for said cyclical heating and cooling;
   whereby heat transfer may oscillate from being directed into the article to being directed out of the article.

9. A device to rapidly and cyclically freeze and thaw fractionable material such as blood, platelets or plasma for use in an operation and as needed comprising, in combination:
   a reservoir adapted to receive heat transfer fluid therein and isolated from the fractionable material by a membrane means, said membrane means interposed between the fractionable material and said reservoir to preclude contact with said heat transfer fluid, and pulsing means to deliver said heat transfer fluid against the transfer fluid fractionable material and through said membrane, said pulsing means and said heat transfer fluid collectively defining a massaging means against the fractionable material to promulgate rapid phase change of the fractionable material by circulating the fractionable material for better heat transfer; and wherein two sumps are provided along with valve means for directing hot heat transfer fluid to one said sump having a heating means therewithin and valve means for directing cold heat transfer fluid to another said sump having a cooling means therewithin.

10. The device of claim 1 wherein said pulsing means delivers said heat transfer fluid at a rate which allows fluid build-up against said membrane, thereby providing hydrostatic pressure which causes said membrane to collapse against the fractionable material, and said reservoir includes drainage means for removing the accumulating said heat transfer fluid; and wherein said fluid is incompressible.

11. The device of claim 9 including means to maintain constant a target temperature for said fractionable material including heating means for said heat transfer fluid set at a temperature coincident with said target temperature for said fractionable material and cooling means for said heat transfer fluid.

12. The device of claim 9 including a sump in said reservoir to receive said heat transfer fluid during the course of its circulation against said membrane, said sump communicating with a sump pump for circulating said heat transfer fluid to said pulsing means, and energy storage means interposed between said pump and a fluid outlet of said pulsing means.

13. The device of claim 12 wherein said energy storage means includes a surge chamber disposed adjacent said pump, downstream therefrom with respect to said sump and a solenoid valve interposed between said sump and said fluid outlet whereby timely opening of said solenoid valve discharges pressure built-up within said surge chamber and induced by said pump to provide added velocity to said thawing fluid as it impinges upon said membrane.

14. The device of claim 9 wherein said pulsing means includes means for synchronizing a plurality of said pulsing means for simultaneous impingement against said membrane.

15. A device to rapidly and cyclically freeze and thaw fractionable material such as blood, platelets or plasma for use in an operation and as needed comprising, in combination:

a reservoir adapted to receive heat transfer fluid therein and isolated from the fractionable material by a membrane means, said membrane means interposed between the fractionable material and said reservoir to preclude contact with said heat transfer fluid, and pulsing means to deliver said heat transfer fluid against the fractionable material and through said membrane, said pulsing means and said heat transfer fluid collectively defining a massaging means against the fractionable material to promulgate rapid phase change of the fractionable material by circulating the fractionable material for better heat transfer;

including means to maintain constant a target temperature for said fractionable material including heating means for said heat transfer fluid set at a temperature coincident with said target temperature for said fractionable material and cooling means for said heat transfer fluid;

wherein said energy storage means includes a surge chamber disposed adjacent said pump, downstream therefrom with respect to said sump and a solenoid valve interposed between said sump and said fluid outlet whereby timely opening of said solenoid valve discharges pressure built-up within said surge chamber and induced by said pump to provide added velocity to said thawing fluid as it impinges upon said membrane; and wherein two sumps are provided along with valve means for directing hot heat transfer fluid to one said sump having said heating means therewithin and valve means for directing cold heat transfer fluid to another said sump having said cooling means therewithin.

* * * * *